(12) United States Patent
Abelman et al.

(10) Patent No.: US 7,951,813 B2
(45) Date of Patent: May 31, 2011

(54) QUINAZOLINONE DERIVATIVES AS ALDH-2 INHIBITORS

(75) Inventors: Matthew Abelman, Mountain View, CA (US); Michael Organ, Burlington (CA); Jeff Zablocki, Los Altos, CA (US); Wing Ming Keung, Wayland, MA (US); Guoxin Tao, Brighton, MA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 12/062,431

(22) Filed: Apr. 3, 2008

(65) Prior Publication Data
US 2008/0249116 A1 Oct. 9, 2008

Related U.S. Application Data

(60) Provisional application No. 60/910,329, filed on Apr. 5, 2007.

(51) Int. Cl.
*A61K 31/517* (2006.01)
(52) U.S. Cl. ................. 514/266.3; 544/287; 548/131
(58) Field of Classification Search ............. 514/266.3; 544/287; 548/131
See application file for complete search history.

(56) References Cited

U.S. PATENT DOCUMENTS

| | | | |
|---|---|---|---|
| 5,204,369 | A | 4/1993 | Vallee et al. |
| 5,624,910 | A | 4/1997 | Vallee et al. |
| 5,886,028 | A | 3/1999 | Vallee et al. |
| 6,121,010 | A | 9/2000 | Vallee et al. |
| 6,255,497 | B1 | 7/2001 | Vallee et al. |
| 7,368,434 | B2 | 5/2008 | Keung et al. |
| 2005/0182045 | A1 | 8/2005 | Nagase et al. |
| 2007/0270332 | A1 | 11/2007 | Vallee et al. |
| 2008/0032995 | A1 | 2/2008 | Zablocki et al. |

FOREIGN PATENT DOCUMENTS

| | | |
|---|---|---|
| WO | WO-93/00896 A1 | 1/1993 |
| WO | WO-03/106435 A1 | 12/2003 |
| WO | WO-2005/032488 A2 | 4/2005 |

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Keung, W. et al. (1993) "Daidzin and Daidzein Suppress Free-choice Ethanol Intake by Syrian Golden Hamsters" *Proc. Natl. Acad. Sci. USA* (90): 10008-10012.
Int'l. Search Report mailed Sep. 9, 2008, Int'l. Application No. PCT/US2008/059304; Filing Date Apr. 3, 2008.

* cited by examiner

*Primary Examiner* — James O Wilson
*Assistant Examiner* — Douglas M Willis
(74) *Attorney, Agent, or Firm* — Brian Lewis; Gilead Sciences, Inc.

(57) ABSTRACT

Disclosed are novel quinazolinone derivatives of formula:

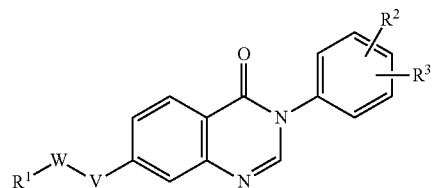

Formula I wherein:
$R^1$ is optionally substituted phenyl or optionally substituted heteroaryl;
$R^2$ is 3-hydroxy, 4-hydroxy, 3-$NHR^4$ or 4-$NHR^4$, in which $R^4$ is hydrogen, —C(O)$R^5$, —C(O)$NHR^6$, or —$SO_2R^6$; in which
$R^5$ is optionally substituted lower alkyl or optionally substituted lower alkoxy; and
$R^6$ is optionally substituted lower alkyl;
$R^3$ is hydrogen, lower alkyl, lower alkoxy, or halo;
V is oxygen, sulfur, or —NH—; and
W is lower alkylene of 1-3 carbon atoms,
which are useful as ALDH-2 inhibitors for treating mammals for various disease states, such as treatment for cocaine dependency and alcohol dependency.

12 Claims, No Drawings

QUINAZOLINONE DERIVATIVES AS ALDH-2 INHIBITORS

This Application claims priority to U.S. Provisional Patent Application Ser. No. 60/910,329, filed Apr. 5, 2007, the complete disclosure of which is hereby incorporated by reference.

FIELD OF THE INVENTION

The present invention relates to quinazolinone derivatives that are ALDH-2 inhibitors, and to their use in treating mammals for various disease states, such as obesity, addiction to alcohol, addiction to cocaine, and addiction to tobacco. The invention also relates to methods for the preparation of such compounds, and to pharmaceutical compositions containing them.

BACKGROUND

Today, dependence upon drugs of addiction causes major health problems worldwide. For example, alcohol abuse and alcohol dependency can cause liver, pancreatic and kidney disease, heart disease, including dilated cardiomyopathy, polyneuropathy, internal bleeding, brain deterioration, alcohol poisoning, increased incidence of many types of cancer, insomnia, depression, anxiety, and even suicide. Heavy alcohol consumption by a pregnant mother can also lead to fetal alcohol syndrome, which is an incurable condition. Additionally, alcohol abuse and alcohol dependence are major contributing factors for head injuries, motor vehicle accidents, violence and assaults, and other neurological and other medical problems.

Another major health problem is caused by cocaine abuse. Physical effects of cocaine use include constricted blood vessels, dilated pupils, and increased temperature, heart rate, and blood pressure. A user of cocaine can experience acute cardiovascular or cerebrovascular emergencies, such as a heart attack or stroke, potentially resulting in sudden death. Other complications associated with cocaine use include disturbances in heart rhythm, chest pain and respiratory failure, seizures and headaches, and gastrointestinal complications such as abdominal pain and nausea. Because cocaine has a tendency to decrease appetite, many chronic users can become malnourished. Repeated use of cocaine may lead to a state of increasing irritability, restlessness, and paranoia. This can result in a period of full-blown paranoid psychosis, in which the user loses touch with reality and experiences auditory hallucinations.

Moreover, it is well known that the concurrent abuse of cocaine and alcohol is common. It has been found that the combination of cocaine and alcohol exerts more cardiovascular toxicity than either drug alone in humans.

Historically, treating alcohol dependence and cocaine dependence largely involved attempts to persuade patients to withdraw from use of alcohol and/or cocaine voluntarily (behavioral therapy). However, alcohol and cocaine are all highly addictive substances, and dependence upon such drugs can be harder to break and is significantly more damaging than dependence on most other addictive substances. In particular, cocaine dependence is typically seen to be a chronic relapsing disorder.

Accordingly, there has been much interest in the scientific community in attempting to find substances that could be employed to ameliorate alcohol dependency and cocaine dependency. Two compounds that have previously been employed for the treatment of alcohol abuse are known as disulfuram (Antabuse™) and cyanamide. Additionally, it has been recently proposed that disulfuram can be used for the treatment of cocaine dependency (for example, see Bonet et al., Journal of Substance Abuse Treatment, 26 (2004), 225-232).

More recently it has been shown that a compound known as daidzein is effective in suppressing ethanol intake. Daidzein is the major active component obtained from extracts of Radix puerariae, a traditional Chinese medication that suppresses ethanol intake in Syrian golden hamsters. See Keung, W. M. and Vallee, B. L. (1993) Proc. Natl. Acad. Sci. USA 90, 10008-10012 and Keung, W. M., Klyosov, A. A., and Vallee, B. L. (1997) Proc. Natl. Acad. Sci. USA 94, 1675-1679, and U.S. Pat. Nos. 5,624,910 and 6,121,010.

It has been shown that daidzin is an isoflavone of the formula:

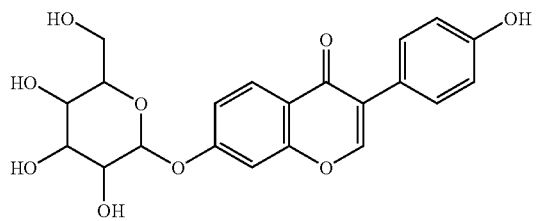

Removal of the sugar provides a compound known as daidzein, which has also been shown to be effective in suppressing ethanol uptake.

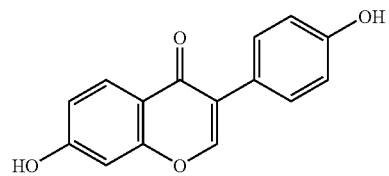

U.S. Pat. Nos. 5,624,910 and 6,121,010 disclosed ether derivatives of daidzin, which were shown to be effective in treating ethanol dependency. Daidzin and its analogs were shown to be potent and selective inhibitors of human mitochondrial aldehyde dehydrogenase (ALDH-2), which is an enzyme involved in the major enzymatic pathway responsible for ethanol metabolism in humans. It was also found that daidzin analogues that inhibit ALDH-2 but also inhibit the monamine oxidase (MOA) pathway were the least effective antidipsotropic activity.

In U.S. Provisional Patent Application Ser. No. 60/834,083 and 60/846,428, novel isoflavone derivatives were disclosed that are ALDH-2 inhibitors with little effect on the MOA pathway, and are useful for the treatment of alcohol dependency and cocaine dependency, and, in particular, ameliorate the tendency of cocaine abusers to relapse.

We have now found quinazolinone derivatives that have similar properties. Surprisingly, it has also been found that ALDH-2 inhibitors, and the quinazolinone derivatives of the invention in particular, are also useful for the treatment of tobacco dependency. Addiction to tobacco is estimated by the National Institute on Drug Abuse to kill nearly 500,000 Americans every year. This total represents about 1 in 6 of all deaths in the U.S. caused by any means, and is more than the total of deaths caused by use of alcohol, cocaine, heroin, suicide, car accidents, fire and AIDS combined. As is well known, the primary addictive component of tobacco is nicotine, which is a highly addictive drug—it activates reward pathways in the brain that regulate feelings of pleasure. That is, nicotine increases levels of the neurotransmitter dopamine in the brain, which provides pleasurable sensations to the smoker.

SUMMARY OF THE INVENTION

Accordingly, in a first aspect, the invention relates to compounds of Formula I:

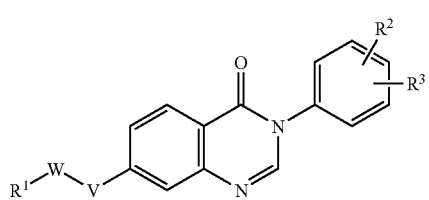

wherein:
$R^1$ is optionally substituted phenyl or optionally substituted heteroaryl;
$R^2$ is 3-hydroxy, 4-hydroxy, 3-$NHR^4$ or 4-$NHR^4$, in which $R^4$ is hydrogen, —C(O)$R^5$, —C(O)$NHR^6$, or —$SO_2R^6$; in which
  $R^5$ is optionally substituted lower alkyl or optionally substituted lower alkoxy; and
  $R^6$ is optionally substituted lower alkyl;
$R^3$ is hydrogen, lower alkyl, lower alkoxy, or halo;
V is oxygen, sulfur, or —NH—; and
W is lower alkylene of 1-3 carbon atoms.

In a second aspect of the invention, pharmaceutical formulations are provided comprising a therapeutically effective amount of an ALDH-2 inhibitor of Formula I, and at least one pharmaceutically acceptable carrier.

In a third aspect of the invention, methods of using the compounds of Formula I in the treatment of a disease or condition in a mammal that can be treated with an ALDH-2 inhibitor are provided. The method comprises administering to a mammal in need thereof a therapeutically effective dose of a compound of Formula I. Such diseases include, but are not limited to, the treatment of drug addiction, particularly alcohol dependency, cocaine dependency, and nicotine addiction.

Preferred compounds of Formula I include a class in which $R^1$ is optionally substituted phenyl, $R^2$ is 4-hydroxyl, $R^3$ is hydrogen, V is oxygen, and W is methylene. One preferred subclass within this class includes those compounds of Formula I in which $R^1$ is phenyl substituted by carboxyl, carboxylic ester, carboxamido, cyano, particularly monosubstituted compounds in which the substitution is at the 3-position.

In another preferred group, $R^1$ is optionally substituted heteroaryl, particularly where $R^1$ is a five membered heteroaryl ring that includes oxygen and nitrogen atoms, more particularly where $R^1$ is (1,2,4-oxadiazol-3-yl), V is oxygen, W is methylene, preferably where $R^2$ is 4-hydroxy and $R^3$ is hydrogen. Within this group, one preferred subgroup includes those compounds in which $R^1$ is (1,2,4-oxadiazol-3-yl) substituted at the 5-position by phenyl substituted by carboxyl, carboxamido, cyano, halo, or lower alkyl substituted by halo, particularly monosubstituted compounds in which the substitution is at the 3-position and disubstituted compounds in which the substitutions are at the 3,5-positions.

At present, the preferred compounds for use in the invention include, but are not limited to:
3-(4-hydroxyphenyl)-7-[(5-phenyl(1,2,4-oxadiazol-3-yl)) methoxy]-3-hydroquinazolin-4-one;
3-(4-hydroxyphenyl)-7-({5-[3-(trifluoromethyl)phenyl](1,2, 4-oxadiazol-3-yl)}methoxy)-3-hydroquinazolin-4-one;
7-({5-[5-fluoro-3-(trifluoromethyl)phenyl](1,2,4-oxadiazol-3-yl)} methoxy)-3-(4-hydroxyphenyl)-3-hydroquinazolin-4-one;
3-(4-hydroxyphenyl)-7-({5-[4-methoxy-3-(trifluoromethyl) phenyl](1,2,4-oxadiazol-3-yl)} methoxy)-3-hydroquinazolin-4-one;
7-({5-[2,5-bis(trifluoromethyl)phenyl](1,2,4-oxadiazol-3-yl)}methoxy)-3-(4-hydroxyphenyl)-3-hydroquinazolin-4-one;
7-({5-[3,5-bis(trifluoromethyl)phenyl](1,2,4-oxadiazol-3-yl)}methoxy)-3-(4-hydroxyphenyl)-3-hydroquinazolin-4-one;
7-({5-[2-methoxyphenyl](1,2,4-oxadiazol-3-yl)} methoxy)-3-(4-hydroxyphenyl)-3-hydroquinazolin-4-one;
3-(3-{[3-(4-hydroxyphenyl)-4-oxo-3-hydroquinazolin-7-yloxy]methyl}-1,2,4-oxadiazol-5-yl)benzenecarbonitrile;
prop-2-enyl 3-(3-{[3-(4-hydroxyphenyl)-4-oxo-3-hydroquinazolin-7-yloxy]methyl}-1,2,4-oxadiazol-5-yl)benzoate;
3-{[3-(4-hydroxyphenyl)-4-oxo-3-hydroquinazolin-7-yloxy]methyl}benzenecarbonitrile;
3-{[3-(4-hydroxyphenyl)-4-oxo-3-hydroquinazolin-7-yloxy]methyl}benzamide;
methylethyl 3-{[3-(4-hydroxyphenyl)-4-oxo-3-hydroquinazolin-7-yloxy]methyl}benzoate; and
3-{[3-(4-hydroxyphenyl)-4-oxo-3-hydroquinazolin-7-yloxy]methyl} benzoic acid;

DETAILED DESCRIPTION OF THE INVENTION

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having 1, 2, 3, 4, 5, 6, 7, 8, 9, 10, 11, 12, 13, 14, 15, 16, 17, 18, 19 or 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:
1) an alkyl group as defined above, having 1, 2, 3, 4 or 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxyl, carboxalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxyl, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2; or 2) an alkyl group as defined above that is interrupted by 1-10 atoms independently chosen from oxygen, sulfur and NR$_a$—, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or
3) an alkyl group as defined above that has both 1, 2, 3, 4 or 5 substituents as defined above and is also interrupted by 1-10 atoms as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1, 2, or 3 substituents, as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, preferably 1-10 carbon atoms, more preferably 1, 2, 3, 4, 5 or 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "lower alkylene" refers to a diradical of a branched or unbranched saturated hydrocarbon chain, preferably having from 1, 2, 3, 4, 5, or 6 carbon atoms.

The term "lower alkylene" refers to a diradical of a branched or unbranched saturated hydrocarbon chain, preferably having from 1, 2, 3, 4, 5, or 6 carbon atoms.

The term "substituted alkylene" refers to:
(1) an alkylene group as defined above having 1, 2, 3, 4, or 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxyl, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or
(2) an alkylene group as defined above that is interrupted by 1-20 atoms independently chosen from oxygen, sulfur and NR$_n$—, where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or
(3) an alkylene group as defined above that has both 1, 2, 3, 4 or 5 substituents as defined above and is also interrupted by 1-20 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers(—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are optionally substituted alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1-6, preferably 1, double bond (vinyl). Preferred alkenyl groups include ethenyl or vinyl (—CH=CH$_2$), 1-propylene or allyl (—CH$_2$CH=CH$_2$), isopropylene (—C(CH$_3$)=CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxyl, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1-6 sites of acetylene (triple bond) unsaturation. Preferred alkynyl groups include ethynyl, (—C≡CH), propargyl (or prop-1-yn-3-yl, —CH$_2$C≡CH), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxyl, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). Unless otherwise constrained by the definition, all substituents may optionally be further substituted by 1-3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. Unless otherwise constrained by the definition, all substituents may optionally be further substituted by 1-3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may be optionally further substituted by alkyl, carboxyl, carboxyalkyl, aminocarbonyl, hydroxy, alkoxy, halogen, CF$_3$, amino, substituted amino, cyano, or —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

The term "arylene" refers to a diradical of an aryl group as defined above. This term is exemplified by groups such as 1,4-phenylene, 1,3-phenylene, 1,2-phenylene, 1,4'-biphenylene, and the like.

Unless otherwise constrained by the definition for the aryl or arylene substituent, such aryl or arylene groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxyl, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y—Z, in which Y is optionally substituted alkylene and Z is alkenyl, cycloalkenyl, or alkynyl, Unless otherwise constrained by the definition, all substituents may optionally be further substituted by 1-3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "carboxyalkyl" refers to the groups —C(O)O-alkyl or —C(O)O-cycloalkyl, where alkyl and cycloalkyl, are as defined herein, and may be optionally further substituted by alkyl, alkenyl, alkynyl, alkoxy, halogen, CF$_3$, amino, substituted amino, cyano, or —S(O)$_n$R, in which R is alkyl, aryl, or heteroaryl and n is 0, 1 or 2.

The term "cycloalkyl" refers to carbocyclic groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, bicyclo[2.2.1]heptane, 1,3,3-trimethylbicyclo[2.2.1]hept-2-yl, (2,3,3-trimethylbicyclo[2.2.1]hept-2-yl), or carbocyclic groups to which is fused an aryl group, for example indane, and the like.

The term "substituted cycloalkyl" refers to cycloalkyl groups having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxyl, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to a radical derived from an aromatic cyclic group (i.e., fully unsaturated) having 1, 2, 3, 4, 5, 6, 7, 8, 9, 10, 11, 12, 13, 14, or 15 carbon atoms and 1, 2, 3 or 4 heteroatoms selected from oxygen, nitrogen and sulfur within at least one ring. Such heteroaryl groups can have a single ring (e.g., pyridyl or furyl) or multiple condensed rings (e.g., indolizinyl, benzothiazolyl, or benzothienyl). Examples of heteroaryls include, but are not limited to, [1,2,4]oxadiazole, [1,3,4]oxadiazole, [1,2,4]thiadiazole, [1,3,4]thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-oxide and N-alkoxy derivatives of nitrogen containing heteroaryl compounds, for example pyridine-N-oxide derivatives.

Unless otherwise constrained by the definition for the heteroaryl or heteroarylene substituent, such heteroaryl or heterarylene groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxyl, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "heteroaralkyl" refers to a heteroaryl group covalently linked to an alkylene group, where heteroaryl and alkylene are defined herein. "Optionally substituted heteroaralkyl" refers to an optionally substituted heteroaryl group covalently linked to an optionally substituted alkylene group. Such heteroalkyl groups are exemplified by 3-pyridylmethyl, quinolin-8-ylethyl, 4-methoxythiazol-2-ylpropyl, and the like.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholino, piperidinyl, piperazino, dihydropyridino, and the like.

Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxyl, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—.

The term "thiocarbonyl" refers to a group —C(S)—.

The term "carboxyl" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, prodrugs, hydrates and polymorphs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R—S system. When the compound is a pure enantiomer the stereochemistry at each chiral carbon may be specified by either R or S. Resolved compounds whose absolute configuration is unknown are designated (+) or (−) depending on the direction (dextro- or laevorotary) which they rotate the plane of polarized light at the wavelength of the sodium D line.

"Parenteral administration" is the systemic delivery of the therapeutic agent via injection to the patient.

The term "therapeutically effective amount" refers to that amount of a compound of Formula I that is sufficient to effect treatment, as defined below, when administered to a mammal in need of such treatment. The therapeutically effective amount will vary depending upon the specific activity of the therapeutic agent being used, and the age, physical condition, existence of other disease states, and nutritional status of the patient. Additionally, other medication the patient may be receiving will effect the determination of the therapeutically effective amount of the therapeutic agent to administer.

The term "treatment" or "treating" means any treatment of a disease in a mammal, including:
(i) preventing the disease, that is, causing the clinical symptoms of the disease not to develop;
(ii) inhibiting the disease, that is, arresting the development of clinical symptoms; and/or
(iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Nomenclature

The naming and numbering of the compounds of the invention is illustrated with a representative compound of Formula I in which $R^1$ is m-benzoic acid, $R^2$ is 4-hydroxy, $R^3$ is hydrogen, V is oxygen, and W is methylene:

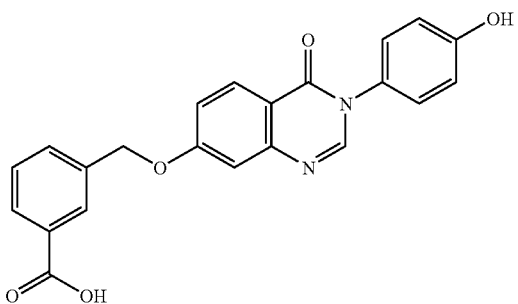

namely: 3-{[3-(4-hydroxyphenyl)-4-oxo-3-hydroquinazolin-7-yloxy]methyl}benzoic acid A compound of Formula I in which $R^1$ is 3-fluoro-5-(trifluoromethyl)phenyl]-(1,2,4-oxadiazol-3-yl), $R^2$ is 4-hydroxy, $R^3$ is hydrogen, V is oxygen, and W is methylene:

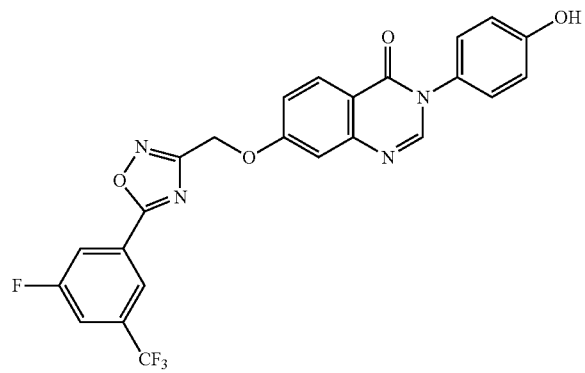

is named 7-({5-[3-fluoro-5-(trifluoromethyl)phenyl](1,2,4-oxadiazol-3-yl)}methoxy)-3-(4-hydroxyphenyl)-3-hydroquinazolin-4-one.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Synthesis of the Compounds of Formula I

The preparation of compounds of Formula I in which $R^2$ is hydroxy starts from 7-hydroxy-3-(4-hydroxyphenyl)-3-hydroquinazolin-4-one, the preparation of which is shown in Reaction Scheme I.

REACTION SCHEME I

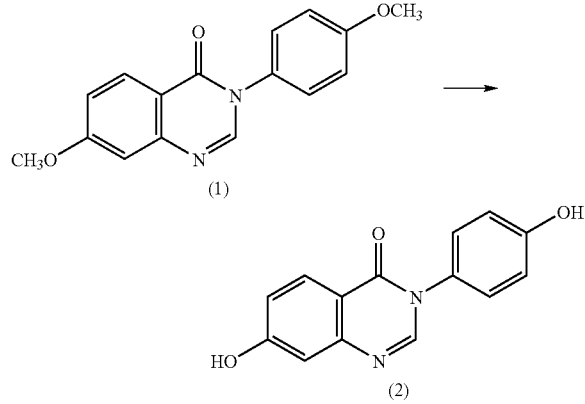

To commercially available 7-methoxy-3-(4-methoxyphenyl)-quinazolin-4(3H)-one (1.0 g, 3.54 mmol) in a dry inert solvent, for example methylene chloride, is added a cleaving agent, for example boron tribromide. The reaction is initially conducted at a temperature of about 0° C., then at about room temperature for about 1-14 days. When the reaction is substantially complete, the product of formula (2) is isolated by conventional means.

The compound of formula (2) is then converted to a compound of Formula I in which $R^2$ is 4-hydroxy as shown in Reaction Scheme II.

REACTION SCHEME II

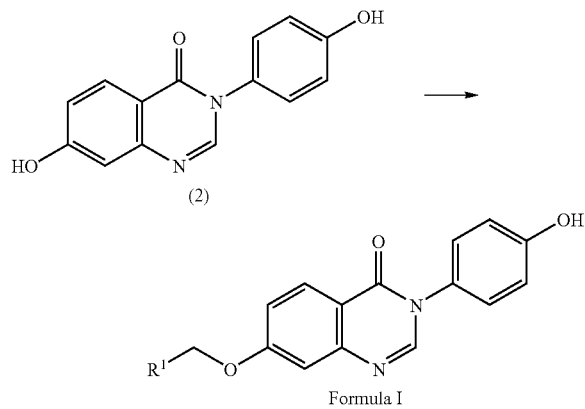

In general, the compound of formula (2), is dissolved in an inert solvent, for example N,N-dimethylformamide, and reacted with about an equimolar amount of a compound of formula $R^1WX$, where W is methylene, ethylene, or propylene, and X is iodo, bromo or chloro, in the presence of a base, for example potassium carbonate, cesium carbonate, or the like. The reaction is conducted at a temperature of about 50-100° C., for about 1-10 hours. When the reaction is substantially complete, the product of Formula I in which $R^2$ is hydroxy is isolated by conventional means, for example by precipitating the product out of solution by addition of water.

Alternatively, the compound of formula (2) is dissolved in an inert solvent, for example acetone, and an aqueous base added, for example 2N potassium hydroxide, and the mixture sonicated for about 5-30 minutes. The mixture is then reacted with about an equimolar amount of a compound of formula $R^1CH_2X$, where X is iodo, bromo or chloro, in the presence of about an equimolar amount of potassium iodide, and the mixture reacted at about reflux temperature for about 1-5 days. When the reaction is substantially complete, the product of Formula I in which $R^2$ is hydroxy is isolated by conventional means, for example by chromatography.

Compounds of Formula I in which $R^2$ is —$NHR^5$ in which $R^5$ is hydrogen may be prepared from an intermediate having a nitro group precursor, as shown in Reaction Scheme III.

REACTION SCHEME III

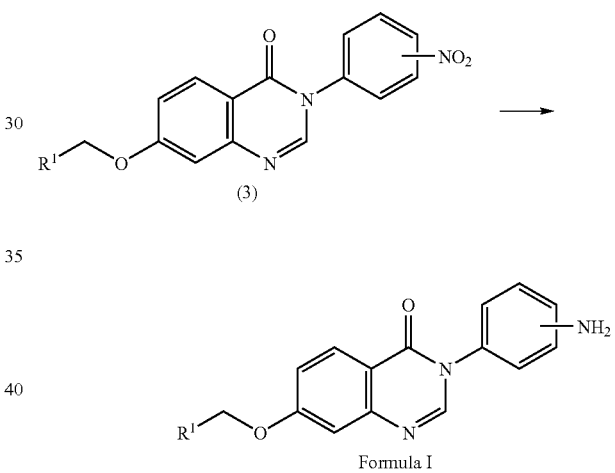

Step 1—Preparation of a Compound of Formula I

In general, a nitro derivative of formula (3) is suspended in an aqueous solvent, for example a mixture of tetrahydrofuran and water, and reacted with sodium dithionite. The reaction is conducted at a temperature of about 50-70° C. overnight. When the reaction is substantially complete, the amine of Formula I is isolated by conventional means, for example by chromatography on silica gel.

It should be noted that if the compound of formula (3) has a carboxyl group present on the $R^1$ moiety, the carboxyl group is better protected as an allyl ester before carrying out the reduction of the nitro group. Such a protecting group protects the carboxyl group in any subsequent reaction in which the amine is, for example acylated, and is easily removed after acylation, whereas an alkyl ester is more difficult to hydrolyze under conventional hydrolysis conditions.

Conversion of a compound of Formula I in which $R^2$ is $NH_2$ to a compound of Formula I in which $R^2$ is $NHSO_2R^5$ is shown in Reaction Scheme IV.

REACTION SCHEME IV

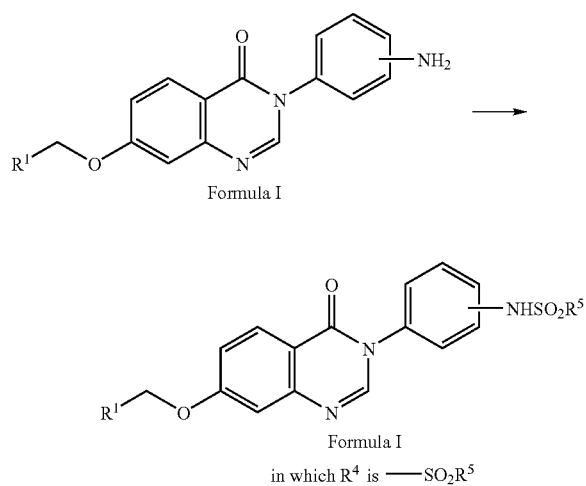

Formula I

Formula I
in which R⁴ is —SO₂R⁵

In general, the compound of Formula I in which $R^2$ is amino is suspended in an inert solvent, for example dichloromethane, and a tertiary base added, for example pyridine. The mixture is cooled to about compound of formula $R^5SO_2Cl$ added, and the mixture reacted for about 1-2 hours. When the reaction is substantially complete, the compound of Formula I in which $R^4$ is —$SO_2R^5$ is isolated by conventional means, for example by chromatography on silica gel.

Similarly, reaction of a compound of Formula I in which $R^2$ is amino with an acylating agent of formula $ClC(O)R^5$ provides compounds of Formula I in which $R^2$ is —$NHR^4$ where $R^4$ is —$C(O)R^5$. Reaction with a compound of formula $ClC(O)NHR^5$ or $R^5NCO$ provides compounds of Formula I in which $R^4$ is —$C(O)NHR^5$.

A convenient synthesis of preparing compounds of Formula I in which $R^1$ is a carboxylic acid is shown in Reaction Scheme V.

In general, an allyl ester derivative of Formula I is dissolved in an inert solvent, for example tetrahydrofuran, and a base, for example morpholine, and tetrakis(triphenyl-phosphine)palladium(0) added. The reaction is conducted at about room temperature for about 1-12 hours. When the reaction is substantially complete, the compound of Formula I in which $R^1$ is a benzoic acid derivative is isolated by conventional means, for example by flash chromatography on silica gel.

Utility, Testing and Administration

General Utility

The compounds of Formula I are effective in the treatment of conditions that respond to administration of ALDH-2 inhibitors. Such conditions include, but are not limited to, alcohol dependency.

Testing

Activity testing is conducted as described in those patents and patent applications referenced above, and in the Examples below, and by methods apparent to one skilled in the art.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17$^{th}$ Ed. (1985) and

REACTION SCHEME V

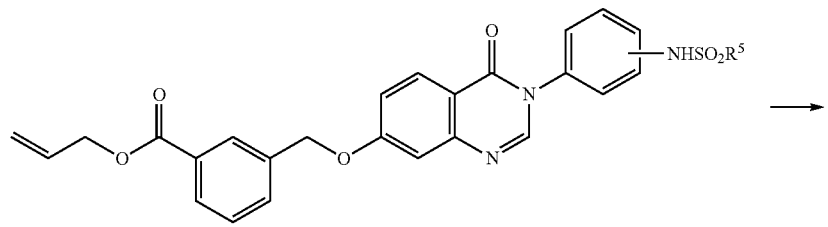

Formula I in which R¹ is an allyl ester derivative

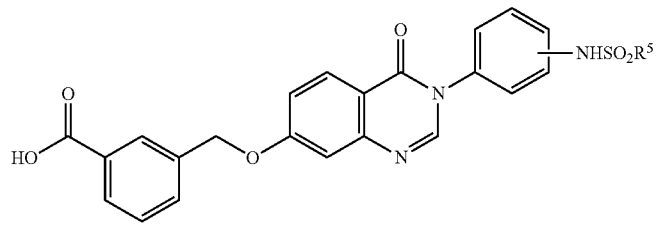

Formula I in which R¹ is a benzoic acid derivative

"Modern Pharmaceutics", Marcel Dekker, Inc. 3rd Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and is generally administered in a pharmaceutically effective amount. Preferably, for oral administration, each dosage unit contains from 10 mg to 2 g of a compound of Formula I, more preferably from 10 to 700 mg, and for parenteral administration, preferably from 10 to 700 mg of a compound of Formula I, more preferably about 50-200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula (2)

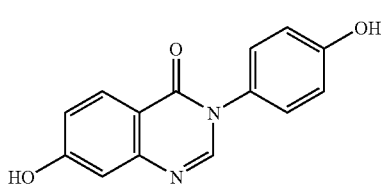

(2)

To a suspension of 7-methoxy-3-(4-methoxyphenyl)-3-hydroquinazolin-4-one (1.0 g, 3.54 mmol) in dry methylene chloride (20 ml) at 0° C. was added boron tribromide (17.7 g, 6.6 ml, 71 mmol). The reaction was stirred at 0° C. for 30 minutes and then at room temperature for 11 days. The reaction mixture was poured slowly into an aqueous saturated solution of sodium bicarbonate (300 mL) and stirred at room temperature for 1 hour. The resulting precipitate was allowed to settle, then filtered off. The solid was washed with water (twice) and dried overnight in vacuo over $P_2O_5$ to give 7-hydroxy-3-(4-hydroxyphenyl)-3-hydroquinazolin-4-one as a brown solid (0.88 g, 98%).

$^1$H NMR (400 MHz, DMSO-$d_6$) δ: 10.59 (br s, 1H), 9.80 (br s, 1H), 8.17 (s, 1H), 8.01 (d, 1H, J=8.5 Hz), 7.27 (d, 2H, J=8.3 Hz), 7.01 (d, 1H, J=8.5 Hz), 6.97 (s, 1H), 6.89 (d, 2H, J=8.3 Hz). LC/MS analysis: $t_R$=6.08 min (isocratic, 65% B), (ESI) m/z 255 (M+H)$^+$.

EXAMPLE 2

A. Preparation of a Compound of Formula I in which $R^1$ is 3-Allylbenzoate, $R^2$ is 4-Hydroxy, $R^3$ is Hydrogen, W is Methylene, and V is Oxygen

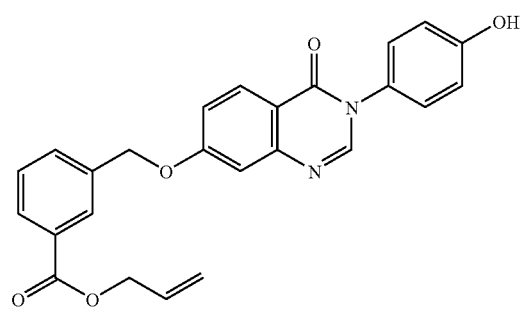

A mixture of 7-hydroxy-3-(4-hydroxyphenyl)quinazolin-4(3H)-one (0.38 g, 1.49 mmol), allyl 3-(chloromethyl)benzoate (0.315 g, 1.49 mmol) and potassium carbonate (0.227 g, 1.64 mmol) in dimethylformamide (5 ml) was heated at 80° C. for 4.5 hours. Solvent was removed under reduced pressure and the residue was dissolved in 1,4-dioxane, mixed with silica gel, concentrated and then isolated with flash column chromatography, eluting with dichloromethane/methanol (92/8) to give prop-2-enyl 3-{[3-(4-hydroxyphenyl)-4-oxo-3-hydroquinazolin-7-yloxy]methyl} benzoate as a white solid (13.3 mg). $IC_{50}$

| hALDH2 | 0.196 µM |
| hMAO-A | No inhibition up to 10 µM |
| hMAO-B | No inhibition up to 10 µM |

B. Preparation of a Compound of Formula I in which $R^1$ is 3-Isopropylbenzoate, $R^2$ is 4-Hydroxy, $R^3$ is Hydrogen, W is Methylene, and V is Oxygen To a suspension of 7-hydroxy-3-(4-hydroxyphenyl)quinazolin-4(3H)-one (100 mg, 0.393 mmol) in acetone (5 ml) was added potassium hydroxide (2N aqueous solution, 0.197 ml, 0.394 mmol), followed by isopropyl 3-(chloromethyl)benzoate (84 mg, 0.393 mmol) and potassium iodide (78 mg, 0.472 mmol). The reaction mixture was refluxed under argon for 48 hours. The reaction was cooled to room temperature, mixed with silica gel, concentrated under reduced pressure, and then isolated with flash column chromatography, eluting with dichloromethane/acetone (90/10) to give methylethyl 3-{[3-(4-hydroxyphenyl)-4-oxo-3-hydroquinazolin-7-yloxy]methyl} benzoate as an off-white solid (44.9 mg).

C. Preparation of Other Compounds of Formula I

Similarly, replacing allyl 3-(chloromethyl)benzoate in Example 1A or isopropyl 3-(chloromethyl)benzoate in Example B with other compounds of formula $R^1$WX, where W is methylene, ethylene, or propylene, and X is iodo, bromo or chloro, and following the procedures of 1A or 1B, the following compounds of Formula I were prepared. 3-(4-hydroxyphenyl)-7-[(5-phenyl(1,2,4-oxadiazol-3-yl))methoxy]-3-hydroquinazolin-4-one;

¹H NMR (400 MHz, DMSO-d₆) δ: 9.82 (s, 1H), 8.27 (s, 1H), 8.16-8.11 (m, 3H), 7.74-7.64 (m, 3H), 7.37 (s, 1H), 7.30-7.28 (m, 3H), 6.89 (d, 2H, J=8.5 Hz), 5.59 (s, 2H).

LC/MS analysis: $t_R$=11.23 min (isocratic, 65% B), (ESI) m/z 413 (M+H)⁺.

| | |
|---|---|
| hALDH2 | 0.107 μM |
| hMAO-A | No inhibition up to 10 μM |
| hMAO-B | No inhibition up to 10 μM |

3-(4-hydroxyphenyl)-7-({5-[3-(trifluoromethyl)phenyl](1,2,4-oxadiazol-3-yl)} methoxy)-3-hydroquinazolin-4-one;

¹H NMR (400 MHz, DMSO-d₆) δ: 9.85 (s, 1H), 8.45 (d, 1H, J=7.7 Hz), 8.39 (s, 1H), 8.28 (s, 1H), 8.12 (d, 2H, J=8.5 Hz), 7.92 (dd, 1H, J=7.8 Hz, J=7.8 Hz), 7.38 (d, 1H, 1.9 Hz), 7.30-7.28 (m, 3H), 6.89 (d, 2H, J=8.6 Hz), 5.62 (s, 2H).

LC/MS analysis: $t_R$=15.02 min (isocratic, 65% B), (ESI) m/z 481 (M+H)⁺.

| | |
|---|---|
| hALDH2 | 0.03 μM |
| hMAO-A | No inhibition up to 10 μM |
| hMAO-B | No inhibition up to 10 μM |

7-({5-[5-fluoro-3-(trifluoromethyl)phenyl](1,2,4-oxadiazol-3-yl)}methoxy)-3-(4-hydroxyphenyl)-3-hydroquinazolin-4-one;

¹H NMR (400 MHz, DMSO-d₆) δ: 9.84 (s, 1H), 8.33 (d, 1H, J=8.3 Hz), 8.28 (s, 1H), 8.25 (s, 1H), 8.17 (d, 1H, J=8.5 Hz), 8.12 (d, 1H, J=8.9 Hz), 7.38 (d, 1H, J=2.0 Hz), 7.30-7.28 (m, 3H), 6.89 (d, 2H, J=8.8 Hz), 5.62 (s, 2H).

LC/MS analysis: $t_R$=16.33 min (isocratic, 65% B), (ESI) m/z 499 (M+H)⁺.

| | |
|---|---|
| hALDH2 | 0.07 μM |
| hMAO-A | No inhibition up to 10 μM |
| hMAO-B | No inhibition up to 10 μM |

3-(4-hydroxyphenyl)-7-({5-[4-methoxy-3-(trifluoromethyl)phenyl](1,2,4-oxadiazol-3-yl)} methoxy)-3-hydroquinazolin-4-one;

¹H NMR (400 MHz, DMSO-d₆) δ: 9.82 (s, 1H), 8.42 (d, 1H, J=8.5 Hz), 8.27 (s, 2H), 8.12 (d, 1H, J=8.9 Hz), 7.55 (d, 1H, J=8.8 Hz), 7.37 (d, 1H, J=2.3 Hz), 7.30-7.28 (m, 3H), 6.89 (d, 2H, J=8.4 Hz), 5.57 (s, 2H), 4.03 (s, 3H).

LC/MS analysis: $t_R$=14.58 min (isocratic, 65% B), (ESI) m/z 511 (M+H)⁺.

| | |
|---|---|
| hALDH2 | 0.1 μM |
| hMAO-A | No inhibition up to 10 μM |
| hMAO-B | No inhibition up to 10 μM |

7-({5-[2,5-bis(trifluoromethyl)phenyl](1,2,4-oxadiazol-3-yl)}methoxy)-3-(4-hydroxyphenyl)-3-hydroquinazolin-4-one;

¹H NMR (400 MHz, DMSO-d₆) δ: 9.82 (s, 1H), 8.52 (s, 1H), 8.37-8.31 (m, 2H), 8.28 (s, 1H), 8.13 (d, 1H, J=8.9 Hz), 7.39 (d, 1H, J=1.9 Hz), 7.30-7.28 (m, 3H), 6.89 (d, 2H, J=8.8 Hz), 5.66 (s, 2H).

LC/MS analysis: $t_R$=17.10 min (isocratic, 65% B), (ESI) m/z 549 (M+H)⁺.

| | |
|---|---|
| hALDH2 | 0.312 μM |
| hMAO-A | No inhibition up to 10 μM |
| hMAO-B | No inhibition up to 10 μM |

7-({5-[3,5-bis(trifluoromethyl)phenyl](1,2,4-oxadiazol-3-yl)}methoxy)-3-(4-hydroxyphenyl)-3-hydroquinazolin-4-one;

¹H NMR (400 MHz, DMSO-d₆) δ: 9.85 (s, 1H), 8.69 (s, 2H), 8.56 (s, 1H), 8.28 (s, 1H), 8.13 (d, 1H, J=8.9 Hz), 7.39 (d, 1H, J=2.0 Hz), 7.30-7.27 (m, 3H), 6.89 (d, 2H, J=9.0 Hz), 5.64 (s, 2H).

LC/MS analysis: $t_R$=20.77 min (isocratic, 65% B), (ESI) m/z 549 (M+H)⁺.

| | |
|---|---|
| hALDH2 | 0.07 μM |
| hMAO-A | No inhibition up to 10 μM |
| hMAO-B | No inhibition up to 10 μM |

7-({5-[2-methoxyphenyl](1,2,4-oxadiazol-3-yl)}methoxy)-3-(4-hydroxyphenyl)-3-hydroquinazolin-4-one;

¹H NMR (400 MHz, DMSO-d₆) δ: 9.84 (s, 1H), 8.27 (s, 1H), 8.12 (d, 1H, J=8.8 Hz), 8.02 (d, 1H, J=7.3 Hz), 7.69 (dd, 1H, J=7.4 Hz, J=8.0 Hz), 7.37-7.27 (m, 5H), 7.12 (dd, 1H, J=7.5 Hz, J=7.5 Hz), 6.89 (d, 2H, J=8.5 Hz), 5.57 (s, 2H), 3.94 (s, 3H). LC/MS analysis: $t_R$=9.87 min (isocratic, 65% B), (ESI) m/z 443 (M+H)⁺.

| | |
|---|---|
| hALDH2 | 0.09 μM |
| hMAO-A | No inhibition up to 10 μM |
| hMAO-B | No inhibition up to 10 μM |

3-(3-{[3-(4-hydroxyphenyl)-4-oxo-3-hydroquinazolin-7-yloxy]methyl}-1,2,4-oxadiazol-5-yl)benzenecarbonitrile;

¹H NMR (400 MHz, DMSO-d₆) δ: 9.82 (s, 1H), 8.58 (s, 1H), 8.45 (d, 1H, J=8.0 Hz), 8.27 (s, 1H), 8.20 (d, 1H, J=8.0 Hz), 8.12 (d, 1H, J=8.8 Hz), 7.87 (dd, 1H, J=7.9 Hz, J=7.8 Hz), 7.38 (d, 1H, J=1.9 Hz), 7.30-7.27 (m, 3H), 6.89 (d, 2H, J=7.4 Hz), 5.61 (s, 2H).

LC/MS analysis: $t_R$=9.48 min (isocratic, 65% B), (ESI) m/z 438 (M+H)⁺.

| | |
|---|---|
| hALDH2 | 25% inhibition at 1 μM |
| hMAO-A | No inhibition up to 10 μM |
| hMAO-B | No inhibition up to 10 μM | prop-2-enyl 3-(3-{[3-(4-hydroxyphenyl)-4-oxo-3-hydroquinazolin-7-yloxy]methyl}-1,2,4-oxadiazol-5-yl)benzoate;

LC/MS analysis: $t_R$=13.92 min (isocratic, 65% B), (ESI) m/z 429 (M+H)⁺.

3-{[3-(4-hydroxyphenyl)-4-oxo-3-hydroquinazolin-7-yloxy]methyl} benzenecarbonitrile;

¹H NMR (400 MHz, DMSO-d₆) δ: 9.82 (s, 1H), 8.25 (s, 1H), 8.10 (d, 1H, J=9.7 Hz), 7.98 (s, 1H), 7.86-7.83 (m, 2H), 7.65 (dd, 1H, J=7.8 Hz, J=7.6 Hz), 7.30-7.25 (m, 4H), 6.89 (d, 2H, J=8.4 Hz), 5.37 (s, 2H).

LC/MS analysis: $t_R$=9.47 min (isocratic, 65% B), (ESI) m/z 370 (M+H)⁺.

| | |
|---|---|
| hALDH2 | 0.196 μM |
| hMAO-A | No inhibition up to 10 μM |
| hMAO-B | No inhibition up to 10 μM |

3-{[3-(4-hydroxyphenyl)-4-oxo-3-hydroquinazolin-7-yloxy]methyl}benzamide;
$^1$H NMR (400 MHz, DMSO-$d_6$) δ: 9.82 (s, 1H), 8.24 (s, 1H), 8.10 (d, 1H, J=8.9 Hz), 8.01 (s, 2H), 7.85 (d, 1H, J=7.6 Hz), 7.65 (d, 1H, J=7.6 Hz), 7.50 (dd, 1H, J=7.5 Hz, J=7.7 Hz), 7.40 (br s, 1H), 7.29-7.24 (m, 4H), 6.88 (d, 2H, J=8.4 Hz), 5.35 (s, 2H).
LC/MS analysis: $t_R$=6.38 min (isocratic, 65% B), (ESI) m/z 388 (M+H)$^+$.

| | |
|---|---|
| hALDH2 | 0.021 μM |
| hMAO-A | No inhibition up to 10 μM |
| hMAO-B | No inhibition up to 10 μM | methylethyl 3-{[3-(4-hydroxyphenyl)-4-oxo-3-hydroquinazolin-7-yloxy]methyl} benzoate;
$^1$H NMR (400 MHz, DMSO-$d_6$) δ: 9.81 (br s, 1H), 8.25 (s, 1H), 8.12-8.08 (m, 2H), 7.93 (d, 1H, J=7.6 Hz), 7.78 (d, 1H, J=7.4 Hz), 7.57 (dd, 1H, J=7.7 Hz, J=7.6 Hz), 7.29-7.24 (m, 4H), 6.89 (d, 2H, J=8.5 Hz), 5.40 (s, 2H), 5.19-5.14 (m, 1H), 1.33 (d, 6H, J=6.1 Hz).
LC/MS analysis: $t_R$=15.80 min (isocratic, 65% B), (ESI) m/z 431 (M+H)$^+$.

| | |
|---|---|
| hALDH2 | 0.095 μM |
| hMAO-A | No inhibition up to 10 μM |
| hMAO-B | No inhibition up to 10 μM |

D. Preparation of Other Compounds of Formula I

Similarly, replacing allyl 3-(chloromethyl)benzoate in Example 1A or isopropyl 3-(chloromethyl)benzoate in Example B with other compounds of formula R$^1$WX, where W is methylene, ethylene, or propylene, and X is iodo, bromo or chloro, and following the procedures of 1A or 1B, other compounds of Formula I are prepared.

EXAMPLE 3

A. Preparation of a Compound of Formula I in which R$^1$ is 3-Benzoic acide, R$^2$ is 4-Hydroxy, R$^3$ is Hydrogen, W is Methylene, and V is Oxygen

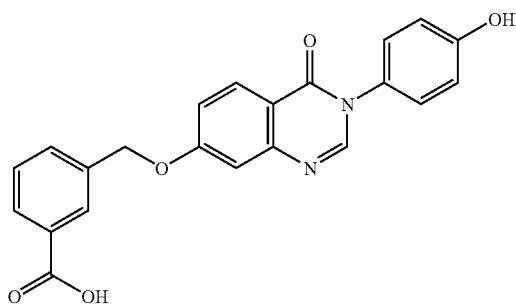

To a suspension of allyl 3-((3,4-dihydro-3-(4-hydroxyphenyl)-4-oxoquinazolin-7-yloxy)methyl)benzoate (117.8 mg, 0.275 mmol), Pd(PPh$_3$)$_4$ (16 mg, 0.014 mmol) in dry tetrahydrofuran (6.0 ml) was added morpholine (120 mg, 1.38 mmol). The reaction was stirred at room temperature under argon for 5 hours. Proton NMR of the reaction mixture showed trace product with most of the starting material. More tetrahydrofuran (6 ml) was added to give a clear solution, then more Pd(PPh$_3$)$_4$ (16 mg, 0.014 mmol) and morpholine (120 mg, 1.38 mmol). The reaction mixture was stirred at room temperature for 48 hours. Proton NMR of the reaction mixture showed no signal for starting material. The reaction mixture was concentrated under reduced pressure, and the residue dissolved in 1,4-dioxane, mixed with silica gel, concentrated and purified with flash column chromatography, eluting with methylene chloride/methanol (92/8), followed by methylene chloride/methanol (92/8) with acetic acid (0.1%) to 85/15 with acetic acid (0.2%), to give 3-{[3-(4-hydroxyphenyl)-4-oxo-3-hydroquinazolin-7-yloxy]methyl}benzoic acid as an off-white solid (86 mg, 78%).
$^1$H NMR (400 MHz, DMSO-$d_6$) δ: 13.1 (br s, 1H), 9.85 (br s, 1H), 8.24 (s, 1H), 8.10-8.07 (m, 2H), 7.92 (d, 1H, J=7.5 Hz), 7.74 (d, 1H, J=7.5 Hz), 7.55 (dd, 1H, J=7.8 Hz, J=7.5 Hz), 7.29-7.25 (m, 4H), 6.88 (d, 2H, J=8.3 Hz), 5.39 (s, 2H).
LC/MS analysis: $t_R$=7.15 min (isocratic, 65% B), (ESI) m/z 389 (M+H)$^+$.

| | |
|---|---|
| hALDH2 | 0.136 μM |
| hMAO-A | No inhibition up to 10 μM |
| hMAO-B | No inhibition up to 10 μM |

EXAMPLE 4

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules.

EXAMPLE 5

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 6

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

EXAMPLE 7

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 8

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 9

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 10

A subcutaneous formulation may be prepared as follows:

| Ingredient | Quantity |
| --- | --- |
| Active Ingredient | 5.0 mg |
| Corn Oil | 1.0 mL |

EXAMPLE 11

An injectable preparation is prepared having the following composition:

| Ingredients | Amount |
| --- | --- |
| Active ingredient | 2.0 mg/ml |
| Mannitol, USP | 50 mg/ml |
| Gluconic acid, USP | q.s. (pH 5-6) |
| water (distilled, sterile) | q.s. to 1.0 ml |
| Nitrogen Gas, NF | q.s. |

EXAMPLE 12

A topical preparation having the following composition:

| Ingredients | grams |
| --- | --- |
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 13

| Sustained Release Composition | | | |
|---|---|---|---|
| Ingredient | Weight Range (%) | Preferred Range (%) | Most Preferred |
| Active ingredient | 50-95 | 70-90 | 75 |
| Microcrystalline cellulose (filler) | 1-35 | 5-15 | 10.6 |
| Methacrylic acid copolymer | 1-35 | 5-12.5 | 10.0 |
| Sodium hydroxide | 0.1-1.0 | 0.2-0.6 | 0.4 |
| Hydroxypropyl methylcellulose | 0.5-5.0 | 1-3 | 2.0 |
| Magnesium stearate | 0.5-5.0 | 1-3 | 2.0 |

The sustained release formulations of this invention are prepared as follows: compound and pH-dependent binder and any optional excipients are intimately mixed (dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl. methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400-600 mg, 650-850 mg, and 900-1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

EXAMPLE 14

MAO and ALDH-2 Assays

The mitochondrial pellet obtained from 5 g of hamster liver was resuspended in 10 mL of 10 mM sodium phosphate buffer (pH 7.4), kept on ice, and sonicated for 3-15 seconds at 90 W of power with a Branson Sonifier cell disruptor. This suspension was centrifuged at 105000 g for 70 min in a Beckman L8 ultracentrifuge and the supernatant, which contained ALDH-2 activity, was used for the ALDH-2 assay. The pellet, which contained mainly mitochondrial membrane, was washed 3 times in 30 mL TKK buffer (10 mM Tris, 10 mM KCl, and 10 mM KPi, pH 7.4). The final pellet, which contained only MAO but not ALDH-2 activity, was used for MAO assay. ALDH-2 activity was assayed in 0.1 M NaPPi, pH 9.5, containing 0.15 M KCl, 1.2 mM NAD+, 0.6 mM formaldehyde, and specified concentrations of daidzin or its structural analogues. Activity was determined by following the increase in absorbance at 340 nm with a Varian Cary 1 spectrophotometer at 25° C.23 MAO activity was assayed in TKK buffer containing 10 iM 5-HT, 0.4 mM sodium bisulfite, specified concentrations of daidzin or its structural analogues, and MAO. Enzyme reaction was initiated by the addition of enzyme and was allowed to proceed at 37° C. for 30 min. The reaction was terminated by centrifugation at 4° C. in a Sorvall Microspin at top speed for 15 min. The reaction product 5-HIAL, present in the supernatant as its stable bisulfite complex, was liberated by diluting the supernatant 10-100-fold in 50 mM NaPPi, pH 8.8 and analyzed by HPLC. Since 5-HIAL is relatively unstable at alkaline pH, 5-HIAL was liberated not more than 4 h before HPLC analysis. The overall recovery of 5-HIAL and 5-HIAA in assay samples spiked with standard analytes were 0.78 and 0.86, and the intra-assay coefficient of variation of the analytical methods determined with samples spiked with 2 iM of the respective analytes are 11.2% and 7.5%. Effect of daidzin and its analogues on ALDH-2 and MAO activities is expressed as: percent (%) inhibition)=(Ao−Ae)×100/Ao, where Ao and Ae are enzyme activities measured in the absence and presence of a test compound, respectively.

EXAMPLE 15

Reduction of Alcohol Dependency

Animals

The strains of alcohol-preferring rats are housed individually in stainless-steel wire mesh cages (26' 34' 20 cm) under constant temperature of 21±1° C. and reversed 12 hour light-12 hour dark cycle (10:00-22:00 dark). These rats consume significantly more alcohol than their respective control strains: the selectively-bred alcohol non-preferring (NP), the low alcohol-drinking (LAD) rat, and the Wistar rat. The FH and P rats were derived from the Wistar rat. Water and food (Agway Prolab Rat/Mouse/Hamster 3000 formula, Agway, Syracuse, USA) were provided ad lib.

Establishment of Baseline

Following the standard method (Murphy et al., 1988; Rezvani and Grady, 1994; Rezvani et al., 1995), alcohol-preferring rats are given 1 day access to water in a Richter tube followed by 3 days of free access to a solution of 10% (v/v) ethanol given as the only source of fluid. Thereafter, the rats were given a choice between alcohol and water for the remainder of the study. All experiments involve 24 hour free access to food, water, and alcohol in a two-bottle choice paradigm.

Experimental Protocol

After establishment of a stable baseline for alcohol and water intakes, animals are maintained on a continuous access to alcohol and water via a two-bottle choice paradigm for about 2 months. Then, rats receive a single i.p. injection of the saline vehicle, or a test compound at 09:30 am. Alcohol and water intakes are measured at 6 and 24 hours after the injection. Food intake is measured 24 hours after the injection.

EXAMPLE 16

Reduction of Cocaine Dependency and Relapse

Intravenous cocaine (0.35 mg/kg/inj) is used in an operant self administration and reinstatement model in rats. In this model, rats addicted to cocaine repeatedly press a lever to obtain an intravenous dose (iv) of cocaine. When cocaine is removed, rats stop pressing the lever. However, rats resume lever pressing for cocaine (reinstatement) if subjected to a small intraperitoneal (ip) dose (10 mg/kg) of cocaine that normally has no effect in naïve animals. This is a valid animal model of relapse in cocaine addicted humans, and tests the ability of compounds of Formula I to block cocaine craving and relapse.

Male Sprague-Dawley rats with jugular vein catheterization are used. Rats are presented with a choice of two levers in the test/training chamber. Depression of the active lever results in delivery of a cocaine reinforcer, while depression of the inactive lever does not result in reinforcement. During the initial 15 hour fixed ratio (FR) 1 training session (FR1 stands for one lever press equals one reinforcement delivery), a food pellet is taped to the active lever to facilitate lever pressing, and each active lever press results in the delivery of a single 45 mg food pellet (Noyes, Lancaster, N.H.). The following day the reinforcer is switched to FR1 lever pressing for cocaine (0.35 mg/kg/inj, delivered in 0.27 sec). Cocaine reinforcement is delivered on a modified FR1 schedule such that each drug infusion is accompanied by illumination of a stimulus over the active lever and a 20 second timeout during which active lever presses are counted but do not result in reinforcer delivery. After 20 seconds the stimulus light is turned off and the first lever press again results in drug delivery. Depression of the inactive lever does not have any consequence. Daily training sessions for each group lasts 2 hours, or until a subject earns 200 drug infusions, whichever came first. The subjects remain in drug self-administration training mode until acquisition criterion is met (average presses on the active lever typically vary by <10% over 3 consecutive training days). This typically takes 10-14 days.

Extinction and Reinstatement

For extinction and reinstatement experiments, rats are required to display stable responding (variability not higher than 15% in 2 consecutive sessions) on the FR1 schedule of reinforcement. After achieving this criteria, extinction procedures begin such that lever presses no longer result in delivery of the reinforcer. When average responding across three consecutive extinction sessions falls to 15% of responding during maintenance, subjects are tested for reinstatement. In cocaine-experienced animals, reinstatement is primed with a non-contingent injection of cocaine (10 mg/kg ip) immediately before the reinstatement session. In order to increase statistical power and therefore decrease animal usage, a second extinction period is initiated 3-4 days after the first, which allows for additional within-subjects comparisons. Experiments use a between-session-training and testing method in which animals are trained to self administer drug. Their behavior is then extinguished and then reinstatement primed on different days.

EXAMPLE 17

Reduction of Tobacco Dependency

Biological material: Wistar-derived male rats (250-300 g) are housed in groups of two and maintained in a temperature-controlled environment on a 12 hour: 12 hour light cycle (0600 h on-1800 h off), upon arrival in the laboratory. Animals are given free access to food and water during a one-week habituation period to the laboratory. Animals used in the research studies are handled, housed, and sacrificed in accord with the current NIH guidelines regarding the use and care of laboratory animals, and all applicable local, state, and federal regulations and guidelines. Animals are handled daily for several days to desensitize them to handling stress before experimental testing. The cell sizes (n=8) provide reliable estimates of drug effects.

Drug Treatments: The Wistar-derived rats receive several doses of test compound, administered intraperitonealy (i.p.), and a positive control compound, mecamylamine (1.5 mg/kg, subcutaneously (s.c.) is administered 30 minutes prior to SA sessions. Test compound is administered at 2 ml/kg for the 7.5 mg/kg (3.75 mg/ml) and 10 mg/kg (5 mg/ml), doses, and at 3 ml/kg for the 15 mg/kg dose (5 mg/ml). 8-[(1E)-2-(3,4-dimethoxyphenyl)vinyl]-1,3-diethyl-7-methyl-1,3,7-trihydropurine-2,6-dione is administered at a volume of 1 ml/kg. The compounds are dissolved in corn oil (VEH), and sonicated for at least 30-minutes, up to 2 hours prior to administration. Mecamylamine is dissolved in 0.09% isotonic saline and administered at a volume of 1 ml/kg.

Apparatus: Food training and nicotine self-administration takes place in 8 standard Coulbourn operant chambers. Each chamber is housed in a sound-attenuated box. Operant chambers are equipped with two levers, mounted 2 cm above the floor, and a cue light mounted 2 cm above the right lever on the back wall of the chamber. For food training, a food hopper is located 2-cm to the left/right of either lever, in the middle of the back wall. Intravenous infusions are delivered in a volume of 0.1 ml over a one second interval via an infusion pump (Razel, Conn.) housed outside of the sound attenuated chamber.

Food Training: Lever pressing is established as demonstrated by the method of Hyytia et al., (1996). Initially, rats are restricted to 15 grams of food daily (approximately 85% of their free-feeding body weight). After the second day of food restriction, rats are trained to respond for food under a fixed-ratio 1 (FR1) schedule of reinforcement (1 food pellet for each lever press) with a 1 second time-out (TO-1s) after each reinforcement. Training sessions are given twice per day, and TO periods are gradually increased to 20 seconds. Once rats obtain a steady baseline responding at a FR1-TO20s schedule of reinforcement, they are returned to ad libitum food prior to preparation for intravenous jugular catheter implant surgery.

Surgery: Rats are anesthetized with a ketamine/xylazine mixture and chronic silastic jugular catheters are inserted into the external jugular and passed subcutaneously to a polyethylene assembly mounted on the animal's back. The catheter assembly consists of a 13-cm length of silasitic tubing (inside diameter 0.31 mm; outside diameter 0.64 mm), attached to a guide cannula that is bent at a right angle. The cannula is embedded into a dental cement base and anchored with a 2×2 cm square of durable mesh. The catheter is passed subcutaneously from the rats back to the jugular vein where it is inserted and secured with a non-absorbable silk suture. Upon successful completion of surgery, rats are given 3-5 days to recover before self-administration sessions start. During the recovery period, rats remain ad libitum food access, and have catheter lines flushed daily with 30 units/ml of heparinized saline containing 66 mg/ml of Timentin to prevent blood coagulation and infection in the catheters.

Nicotine Self-Administration: Following successful recovery from catheter implant surgery, rats are again food deprived to 85% of their free-feeding body weight. Once self-administration sessions begin, subjects are trained to IV self-administer nicotine in 1-hour baseline sessions, 5 days per week, under a FR1-TO-20 schedule of reinforcement until stable responding is achieved. Stable responding is defined as less than 20% variability across 3 consecutive sessions. After acquisition of stable responding for nicotine, various doses of test compound is tested using a within-subjects Latin square design. Rats are allowed to self-administer each dose of test compound for 1 test session, and subsequently "rebaselined" for 1-3 days before the next dose probe during one test self-administrations sessions. Following the testing of the first compound, rats receive the positive control compound, mecamylamine (1.5 mg/kg), administered according to a crossover design. Following this testing, rats continue to be run under baseline nicotine conditions, and, upon stable responding for nicotine, rats are tested with 8-[(1E)-2-(3,4-dimethoxyphenyl)vinyl]-1,3-diethyl-7-methyl-1,3,7-trihydropurine-2,6-dione and positive control compound, according to the schedule outlined above.

During SA sessions, rats are flushed with saline before test session to ensure catheter patency, and again flushed after test sessions with 30 units/ml of heparinized saline containing 66 mg/ml of Timentin, to prevent blood coagulation and infection in the catheters. If catheter patency is in question, demonstrated by an unexpected shift in response rates, or inability to draw blood from the catheter, 0.1 ml of a short-acting anesthetic (Brevital) should be infused. Animals with patent catheters exhibit rapid loss of muscle tone within 3-seconds. Rats with catheters no longer patent according to the Brevital test are removed from the experiment.

Data Analysis

Data is collected on-line from multiple operant chambers, and reported as mean cumulative number of bar presses for nicotine. The data is analyzed using the StatView statistical package on a PC-compatible computer.

What is claimed is:

1. A compound of the Formula I:

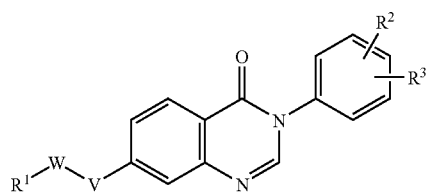

Formula I wherein:
$R^1$ is phenyl optionally substituted by 1, 2 or 3 groups chosen from carboxyl, carboxyalkyl, carboxamido, cyano, halo, and lower alkyl optionally substituted by halo, or $R^1$ is oxadiazolyl optionally substituted by a phenyl group that is optionally substituted by 1, 2 or 3 groups chosen from halogen, cyano, alkoxy of 1-6 carbon atoms, alkynyl of 1-6 carbon atoms, or lower alkyl of 1-6 carbon atoms, which is optionally substituted by hydroxy, 2, or 3 halo atoms, cyano, or cycloalkyl of 4-6 carbon atoms;
$R^2$ is 3-hydroxy, 4-hydroxy, 3—$NHR^4$ or 4—$NHR^4$, in which $R^4$ is hydrogen, —$C(O)R^5$, —$C(O)NHR^6$, or —$SO_2R^6$; in which
$R^5$ is lower alkyl of 1-6 carbon atoms or lower alkoxy of 1-6 carbon atoms; and
$R^6$ is lower alkyl of 1-6 carbon atoms;

$R^3$ is hydrogen, lower alkyl of 1-6 carbon atoms, lower alkoxy of 1-6 carbon atoms, or halo;
V is oxygen, sulfur, or —NH—; and
W is lower alkylene of 1-3 carbon atoms.

2. The compound of claim 1, wherein said optionally substituted phenyl is monosubstituted, W is methylene, $R^2$ is 4-hydroxy, $R^3$ is hydrogen, and V is oxygen.

3. The compound of claim 1, wherein said optionally substituted phenyl is disubstituted, W is methylene, $R^2$ is 4-hydroxy, $R^3$ is hydrogen, and V is oxygen.

4. The compound of claim 2, selected from
3-(4-hydroxyphenyl)-7-[(5-phenyl(1,2,4-oxadiazol-3-yl))methoxy]-3-hydroquinazolin-4-one;
3-(4-hydroxyphenyl)-7-({5-[3-(trifluoromethyl)phenyl](1,2,4-oxadiazol-3-yl)}methoxy)-3-hydroquinazolin-4-one;
7-({5-[2-methoxyphenyl](1,2,4-oxadiazol-3-yl)}methoxy)-3-(4-hydroxyphenyl)-3-hydroquinazolin-4-one; and
3-(3-{[3-(4-hydroxyphenyl)-4-oxo-3-hydroquinazolin-7-yloxy]methyl}-1,2,4-oxadiazol-5-yl)benzenecarbonitrile.

5. The compound of claim 3, selected from
7-({5-[5-fluoro-3-(trifluoromethyl)phenyl](1,2,4-oxadiazol-3-yl)}methoxy)-3-(4-hydroxyphenyl)-3-hydroquinazolin-4-one;
3-(4-hydroxyphenyl)-7-({5-[4-methoxy-3-(trifluoromethyl)phenyl](1,2,4-oxadiazol-3-yl)}methoxy)-3-hydroquinazolin-4-one;
7-({5-[2,5-bis(trifluoromethyl)phenyl](1,2,4-oxadiazol-3-yl)}methoxy)-3-(4-hydroxyphenyl)-3-hydroquinazolin-4-one; and
7-({5-[3,5-bis(trifluoromethyl)phenyl](1,2,4-oxadiazol-3-yl)}methoxy)-3-(4-hydroxyphenyl)-3-hydroquinazolin-4-one.

6. The compound of claim 1, wherein $R^1$ is phenyl optionally substituted by 1, 2 or 3 groups chosen from carboxyl, carboxyalkyl, carboxamido, cyano, halo, or lower alkyl optionally substituted by halo.

7. The compound of claim 6, wherein $R^1$ is monosubstituted phenyl.

8. The compound of claim 6, wherein $R^1$ is disubstituted phenyl.

9. The compound of claim 8, wherein each of said two substituents is independently selected from carboxyl, carboxyalkyl, carboxamido, or cyano.

10. The compound of claim 6, wherein W is methylene, $R^2$ is 4-hydroxy and V is oxygen.

11. The compound of claim 1, selected from
3-{[3-(4-hydroxyphenyl)-4-oxo-3-hydroquinazolin-7-yloxy]methyl}benzenecarbonitrile;
3-{[3-(4-hydroxyphenyl)-4-oxo-3-hydroquinazolin-7-yloxy]methyl}benzamide;
methylethyl 3-{[3-(4-hydroxyphenyl)-4-oxo-3-hydroquinazolin-7-yloxy]methyl}benzoate; and
3-{[3-(4-hydroxyphenyl)-4-oxo-3-hydroquinazolin-7-yloxy]methyl}benzoic acid.

12. A pharmaceutical formulation comprising a therapeutically effective amount of a compound of Formula I, and at least one pharmaceutically acceptable carrier.

* * * * *